United States Patent [19]
Kurosaki et al.

[11] Patent Number: 5,587,129
[45] Date of Patent: Dec. 24, 1996

[54] APPARATUS FOR AUTOMATICALLY ANALYZING SPECIMEN

[75] Inventors: Tsuyoshi Kurosaki; Atsuo Tomioka; Takashi Yamato, all of Hyogo, Japan

[73] Assignee: Toa Medical Electronics Co., Ltd., Hyogo, Japan

[21] Appl. No.: 530,901

[22] Filed: Sep. 20, 1995

[30] Foreign Application Priority Data

Sep. 21, 1994 [JP] Japan ..................... 6-266015

[51] Int. Cl.⁶ ................................. G01N 35/02
[52] U.S. Cl. ..................... 422/64; 422/63; 422/65; 422/67; 436/43; 436/47; 436/48; 436/49; 436/50; 436/54
[58] Field of Search .................. 422/63, 64, 65, 422/67, 73, 100; 436/43, 47, 48, 49, 50, 54, 55, 174, 180

[56] References Cited

U.S. PATENT DOCUMENTS

| | | | |
|---|---|---|---|
| 4,478,095 | 10/1984 | Bradley et al. | 73/864.21 |
| 4,834,944 | 5/1989 | Wakatake | 422/64 |
| 4,965,049 | 10/1990 | Lillig et al. | 422/68.1 |
| 5,051,238 | 9/1991 | Umetsu et al. | 422/64 |
| 5,084,242 | 1/1992 | Sakuma et al. | 422/100 |
| 5,183,638 | 2/1993 | Wakatake | 422/64 |
| 5,242,659 | 9/1993 | Wurschum | 422/65 |
| 5,470,534 | 11/1995 | Imai et al. | 422/67 |
| 5,472,669 | 12/1995 | Miki et al. | 433/63 |
| 5,482,861 | 1/1996 | Clark et al. | 436/48 |

FOREIGN PATENT DOCUMENTS

92/05448  4/1992  WIPO .

Primary Examiner—Long V. Le

[57] ABSTRACT

An apparatus and a method for automatically analyzing specimens are disclosed. The apparatus includes a sample vial retainer for retaining a sample vial containing a specimen such as blood; a stock vial into which part of the specimen in the sample vial is dispensed; a stock vial retainer for retaining the stock vial; a first dispenser for dispensing the specimen in the sample vial to the stock vial; an assay vial into which part of the specimen in the stock vial is dispensed; an assay vial retainer for retaining a plurality of assay vials; a second dispenser for dispensing the specimen in the stock vial to the assay vial; a reagent container for containing a reagent necessary for an assay; a third dispenser for dispensing the reagent to the assay vial; an assay device for assaying the specimen in the assay vial; an assay vial transporter for transporting the assay vial retained in the assay vial retainer to the assay device; a vial discharger for discharging the assay vial after the assay; and a controller, whereby the specimen once dispensed from the sample vial to the stock vial is dispensed from the stock vial to the assay vial for an assay.

13 Claims, 11 Drawing Sheets

APPARATUS FOR AUTOMATICALLY ANALYZING SPECIMEN

BACKGROUND OF THE INVENTION

1. Field of the Invention

The present invention relates to apparatuses and methods for automatically analyzing a specimen and, more particularly, to apparatuses and methods for automatically analyzing a specimen for clinical assays utilizing a blood coagulation reaction and immunoreaction.

2. Description of Related Arts

In clinical assays utilizing a blood coagulation reaction and immunoreaction, measurements are repeatedly performed on a specimen for plural assays, or a so-called reflex test is performed in which, for example, fundamental assays such as for the prothrombin time (PT) and activated partial thromboplastin time (APTT) are first performed on a specimen in a primary screening and the mount of fibrinogen (Fbg) of the specimen is then measured or not measured in a secondary screening depending on the result of the primary screening.

Further, if the result of an assay of a specimen is within a predetermined abnormal value range or out of a predetermined normal value range due to malfunction of an analyzer, deterioration of reagents or the like, the assay has to be performed again on the specimen.

In general, where a re-assay or plural measurements are required to be performed on one specimen, the specimen is dispensed from a particular sample vial to analysis means.

In prior arts, where a plurality of specimens in sample vials placed on a rack are automatically assayed, a particular specimen to be subjected to a re-assay or plural measurements is selectively sampled from the corresponding sample vial and dispensed to the assay means.

However, some assays take several minutes to several dozens minutes, requiring a long time after the dispensing of a specimen to obtain measurement results. Therefore, when it is determined that a particular specimen has to be re-assayed, the rack accommodating a sample vial which contains the specimen may already be transported to the next analyzer.

In such a case, the rack accommodating the sample vial has to be returned to a predetermined position, and then the sample vial which contains the specimen to be re-assayed is searched for. This may require an extra time and, in the worst case, the re-assay may become impossible.

In addition, an apparatus adapted to return a rack accommodating sample vials to a predetermined position for re-assay may be large-scale and complicated, and thereby costly.

Therefore, it is desired to repeatedly use a specimen once taken into an analyzer for re-assay or plural measurements.

SUMMARY OF THE INVENTION

In general, sample vials each containing a specimen are successively transported from one analyzer to another analyzer so that the specimen is subjected to various assays. In accordance with the present invention, when a sample vial is transported to a predetermined position of an analyzer, part of a specimen in the sample vial is once stored in a stock vial preliminarily set in the analyzer, and then a necessary amount of the specimen is dispensed from the stock vial to an assay vial to be assayed. Therefore, where a re-assay is to be performed on the specimen, the specimen stored in the stock vial can be used for the re-assay even if the sample via is transported out of the analyzer. Thus, the construction of the analyzer can be simplified in comparison with a conventional analyzer in which a necessary sample vial is returned to the analyzer every time a re-assay is to be performed and, in addition, the analyzer has an improved assay efficiency.

More specifically, the present invention is to provide an apparatus for automatically analyzing a specimen, comprising sample a vial retaining device for retaining a sample vial containing a specimen; a stock vial into which part of the specimen in the sample vial is to be dispensed; a stock vial retaining device for retaining a stock vial; a first dispensing device for dispensing the specimen in the sample vial into the stock vial; an assay vial into which part of the specimen in the stock vial is to be dispensed; an vial retaining device for retaining a plurality of assay vials; a second dispensing device for dispensing the specimen in the stock vial into the assay vial; a reagent container for containing a reagent necessary for an assay; a third dispensing device for dispensing the reagent into the an vial; assay device for assaying the specimen in the assay vial; an vial transporting device for transporting the assay vial from the assay vial retaining device to the assay device; vial discharging device for discharging the assay vial after the assay; and a controller for controlling the sample vial retaining device, the stock vial retaining device, the first dispensing device, the assay vial retaining device, the second dispensing device, the third dispensing device, the assay device, the assay vial transporting device, and the vial discharging device; whereby the specimen once dispensed from the sample vial into the stock vial is dispensed from the stock vial into the assay vial for the assay. The reagent may be a diluent.

These and other objects of the present invention will become more readily apparent from the detailed description given hereafter. However, it should be understood that the detailed description of the specific examples, while indicating preferred embodiments of the invention are given by way of illustration only, since various changes and modifications within the spirit and scope of the invention will become apparent to the those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENT

In the present invention, a sample vial retaining device transports to transport a sample vial containing a specimen to a predetermined position in an analyzer and thereafter transport the sample vial out of the analyzer. Exemplary specimens to be contained in the sample vial include blood plasma and urine.

Exemplary assay devices include optical measuring apparatuses utilizing a known chromogenic assay method in which the absorbance of a specimen colored by a reagent is measured and a coagulation method in which a coagulation time of a specimen coagulated by a reagent and a change in the scattered light intensity thereof are measured. Accordingly, exemplary reagents to be added to specimens include known color developing agents which react with a specimen for coloration thereof and known coagulation agents which gelatinize a specimen. Via is used for assays are preferably transparent vials that are highly pervious to light to be employed for the assays.

It is essential to use the least amount of a specimen to perform a correct assay on the specimen in the analyzer. In the analyzer of the present invention, the mount T of a specimen to be dispensed into a stock vial is calculated as follows:

$$T=(S1+ \ldots +Sn) \times k + U$$

where S1 to Sn are volumes necessary for respective assays, k is the number of measurements, and U is a spare volume.

In a PT measurement, for example, S=50 µl, k=2, and U=60 µl. Therefore, the mount T of a specimen to be dispensed is 160 µl.

In general, specimens in assay vials which have been treated with reagents are discarded after an assay. In this case, however, the specimens remaining in the stock vials can be returned to the corresponding sample vials by suitable means to be used again for another assay.

The present invention will hereinafter be described by way of an embodiment thereof with reference to the attached drawings. It should be noted that the embodiment is not limitative of the present invention.

Figure 1:
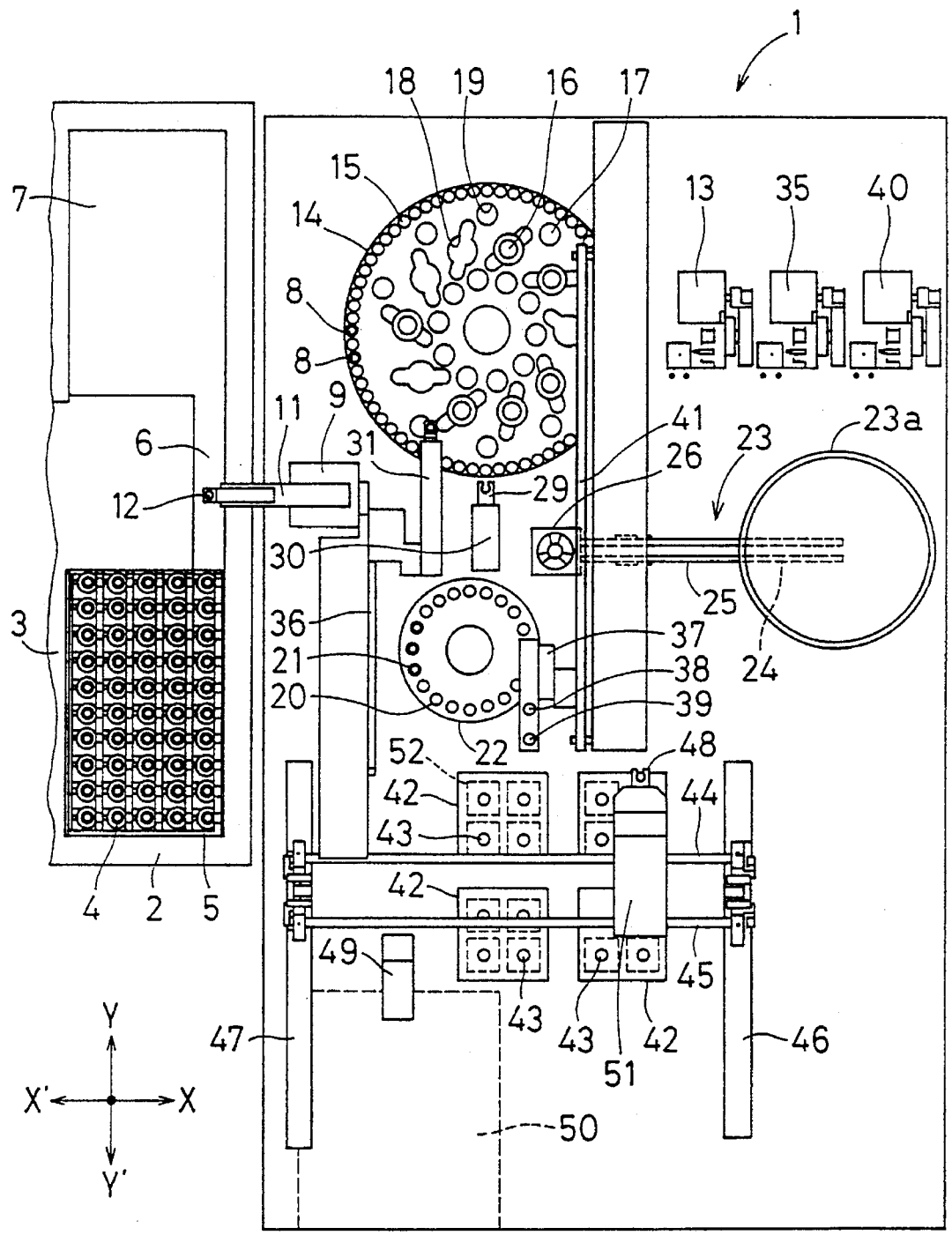
FIG. 1 is a plan view illustrating an automatic specimen analyzer in accordance with one embodiment of the present invention.
Figure 2:
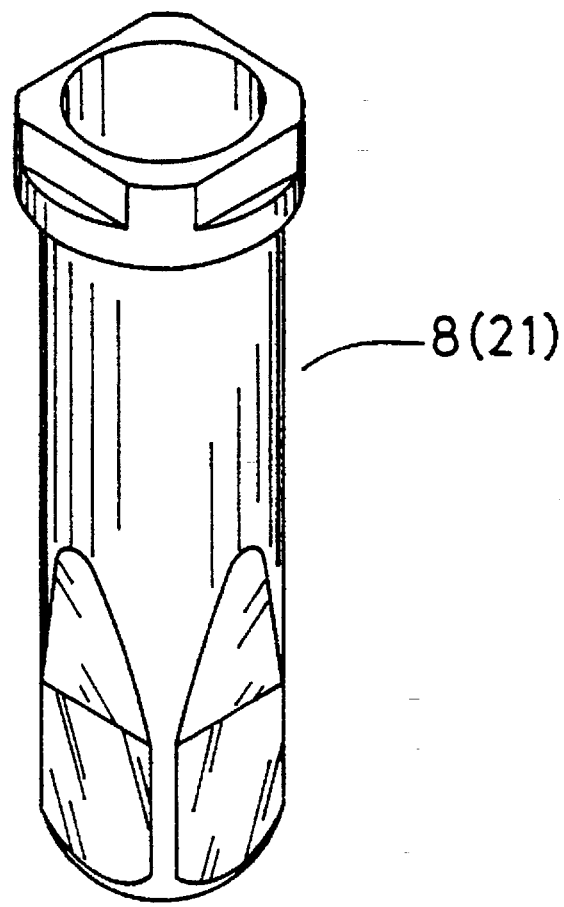
FIG. 2 is a perspective view illustrating a vial used as a stock vial and an assay vial.

FIG. 1 is a plan view illustrating a blood coagulation reaction analyzer Ln accordance with one embodiment of the present invention. FIG. 2 is a perspective view illustrating a vial to be used as a stock vial and an assay vial.

Referring to FIG. 1, the analyzer includes a main body 1 and a rack transportation device 2 disposed at an operation side thereof. Five racks 5 each retaining in line ten sample vials 4 (blood sampling tubes) each of which contains a specimen (blood plasma) are disposed in a parallel relation on a rack supply yard 3 on the rack transportation device 2. Each rack 5 is transported in a direction indicated by arrow Y to a specimen sampling area 6 and then transported to a stock yard 7. In this embodiment, each of the sample vials 4 is tightly capped with a soft rubber stopper.

Figure 3:
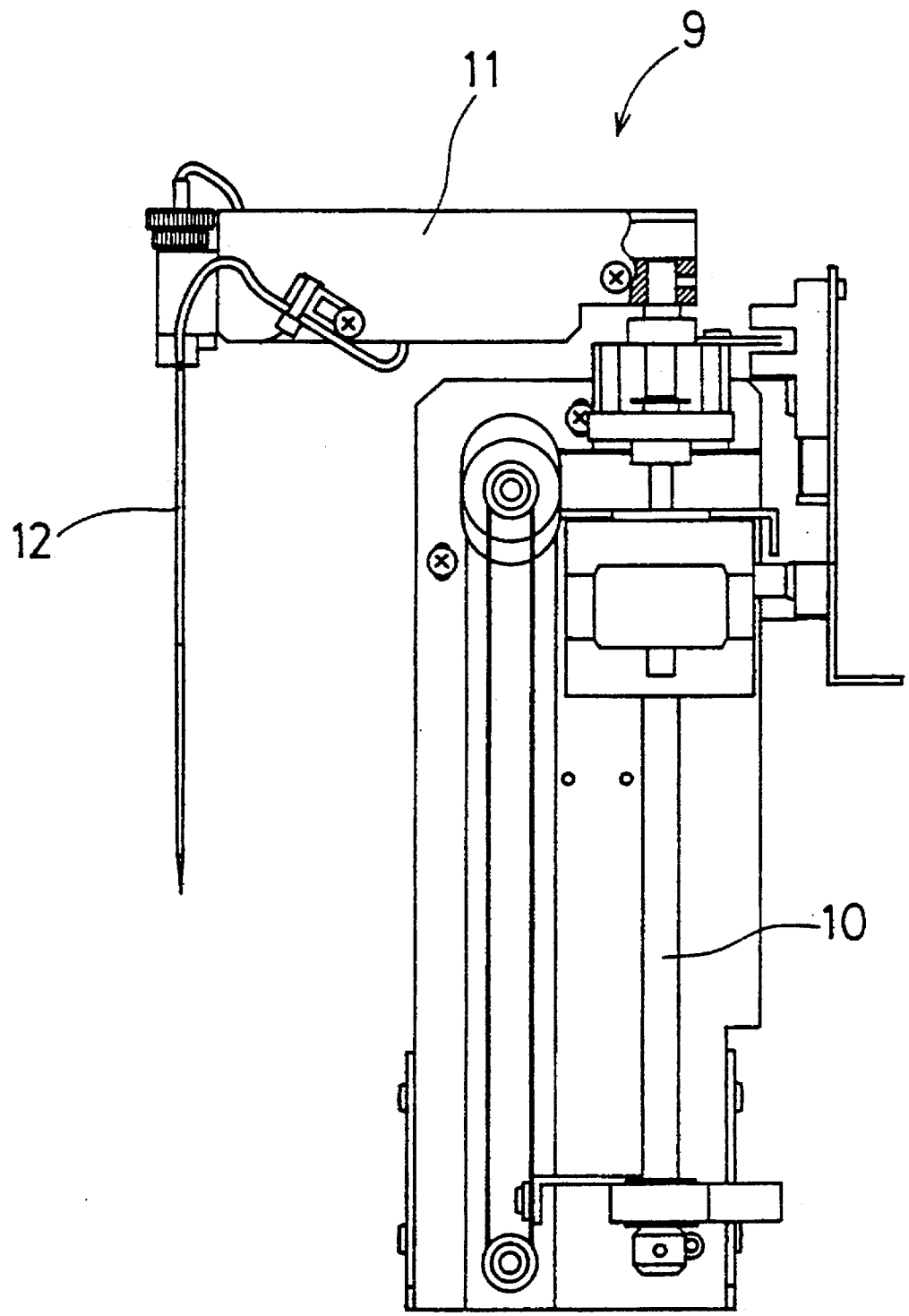
FIG. 3 is a side view illustrating first dispensing means.

A first dispensing device 9 for aspirating part of a specimen in a sample vial 4 and dispersing the specimen into a stock vial 8 is disposed at a location facing opposite to the specimen sampling area 6 of the main body 1. As shown in FIG. 3, the first dispensing device 9 has a pivotally and vertically movable shaft 10, swiveling arm 11 fixed on the top end of the shaft 10, and a sampling probe 12 attached at a free end of the swivel arm 11. The sampling probe 12 is connected to a constant-volume liquid transportation device 13 (FIG. 1) via a tube. The lower end of the sampling probe 12 is formed into a sharp tip like a syringe needle to stick the rubber stopper of the sample vial for the aspiration of the specimen contained in the sample vial 4.

A disk-shaped first turntable 14 is formed with sixty vial retaining holes 15 annularly aligning in a peripheral portion thereof for retaining therein stock vials 8. These vial retaining holes 15 serve as the stock vial retaining device. Reagent container retaining holes 18 and 19 for retaining therein reagent containers 16 and 17 are formed in a portion radially inward from the vial retaining holes 15 concentrically with the vial retaining holes 15.

Below the first turntable 14 is provided a cooling device including a Peltier element for keeping the temperature of specimens contained in the stock vials 8° at 15° C.

A disk-shaped second turntable 20 having a diameter smaller than that of the first turntable 14 (about one half) is formed with twenty to vial retaining holes 22 for retaining therein assay vials 21 (the same type as the stock vials). These vial retaining holes 22 serve as the to assay vial retaining means.

Figure 4:
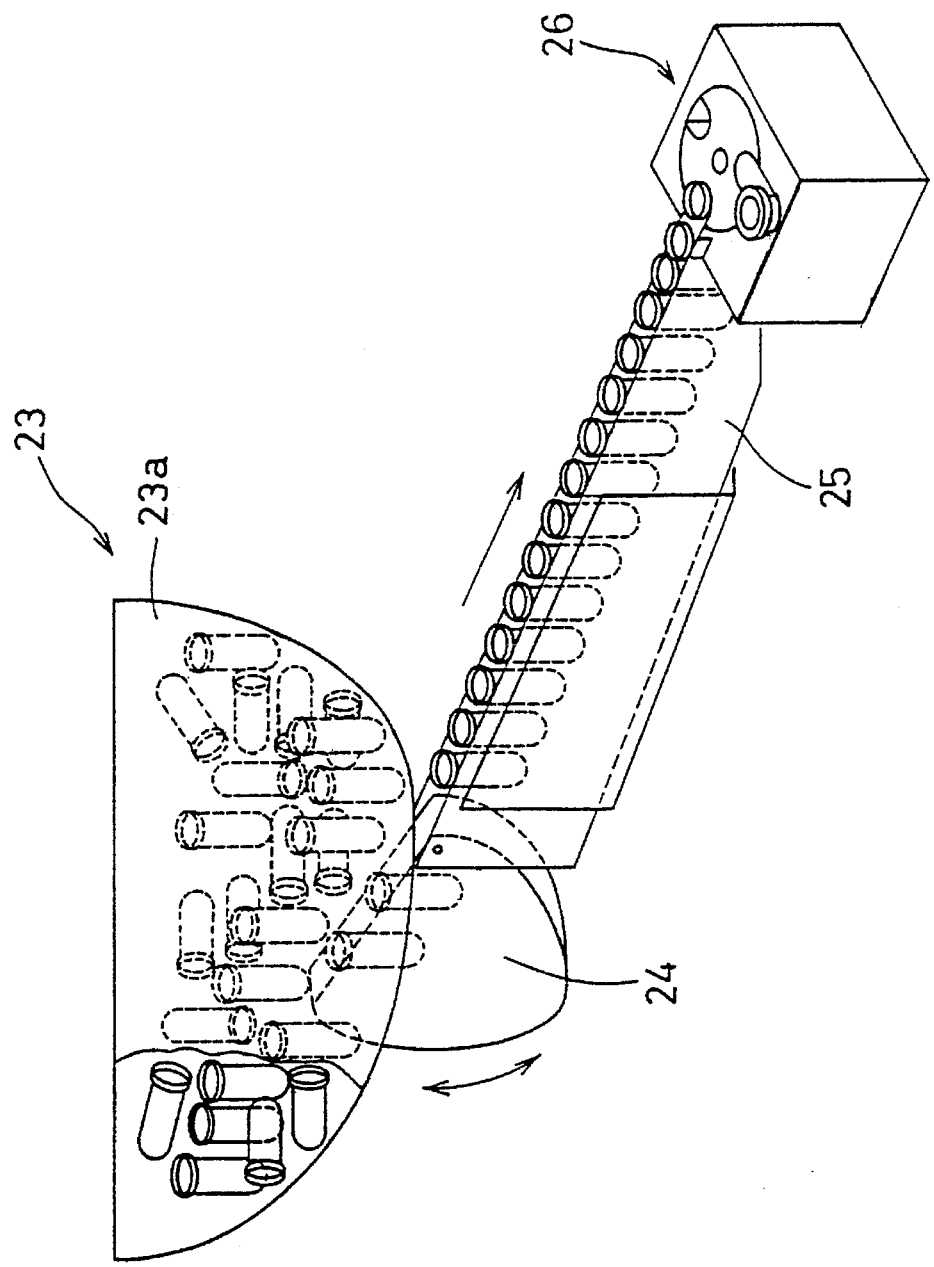
FIG. 4 is a perspective view illustrating a part feeder.

The second turntable 20 is provided with a heater (not shown) for keeping the temperature of specimens contained in the assay vials at 37° C. A part feeder 23 of pivotal rail type for feeding the stock vials 8 and assay vials 21 has a vial storage 23a, and an inclined chute 25 disposed at a feeding end of pivotal rails 24 for transporting the stock vials 8 (assay vials 21) in line with the vials kept vertical as shown in FIG. 4. At a downstream end of the inclined chute 25 is disposed a vial separation device 26. The vial separation device 26 allows the stock vials 8 (assay vials 21) sliding down along the inclined chute 25 to assume a predetermined attitude, and slightly upwardly projects the vial to facilitate the chucking of the vial by a chucking finger (which will be described later).

Figure 5:
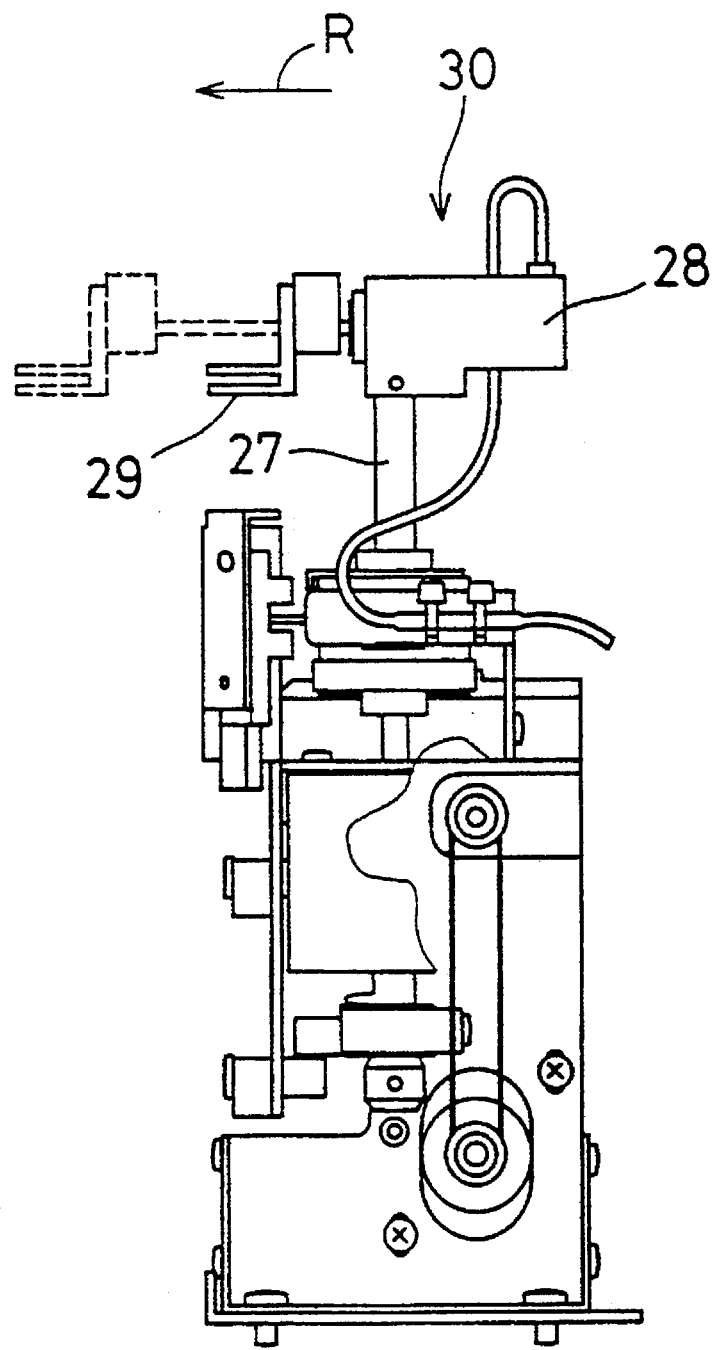
FIG. 5 is a side view illustrating a vial distributing/supplying device.
Figure 11:
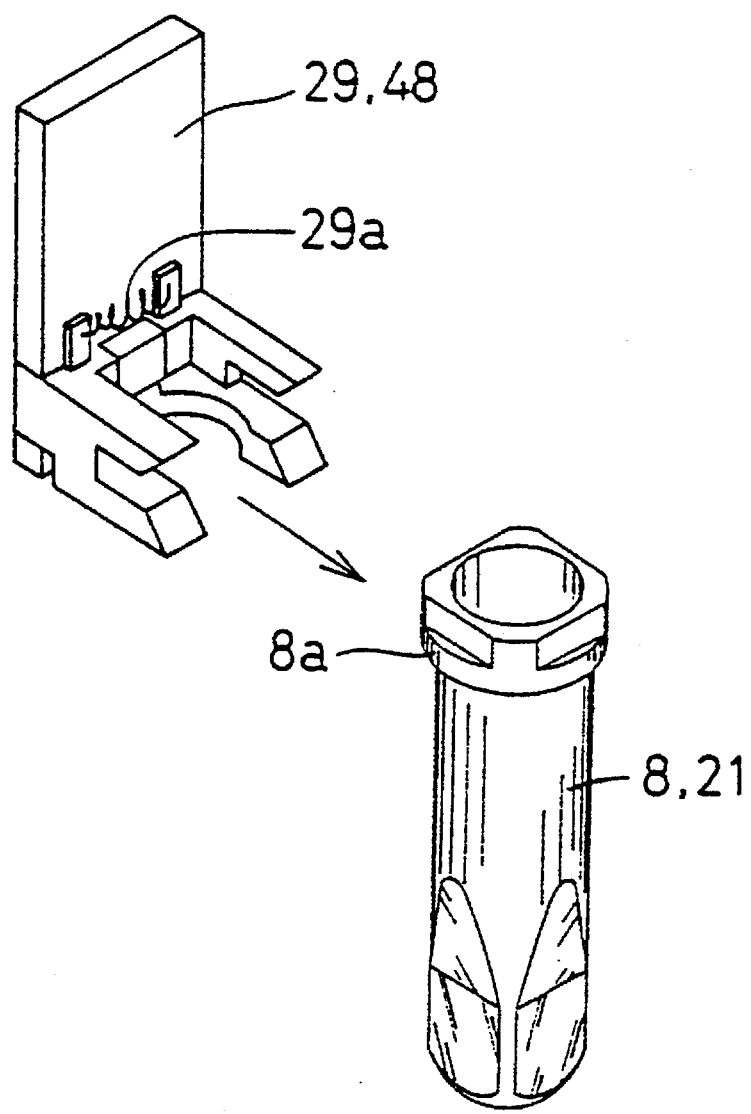
FIG. 11 is a perspective view illustrating a chucking finger.

A vial distributing/supplying device 30 as shown in FIG. 5 is disposed between the first turntable 14 and the second turntable 20, which includes a pivotally and vertically movable shaft 27, a swivel actuator 28 fixed at the top end of the shaft 27 and a chucking finger 29 attached at a free end of the swivel actuator 28. The chucking finger 29 is adapted to resilient y hold a lip portion 8a of the stock vial 8 (assay vial 21) by the force of a spring 29a, as shown in FIG. 11. The swivel actuator 28 incorporates therein an air cylinder for projecting the chucking finger 29 in a direction indicated by arrow R to a position indicated by dotted line in FIG. 5.

The vial distributing/supplying device 30 transports the stock vial 8 or assay vial 21 supplied by the vial separation device 26 into the vial retaining hole 15 of the first turntable 14 or the vial retaining hole 22 of the second turntable 20 by holding the lip portion of the stock vial 8 or assay vial 21 by means of the chucking finger 29. More specifically, when the swivel actuator 28 swivels counterclockwise from a vial chucking position of the vial separation device 26 (see FIG. 1 ), the stock vial 8 is supplied to the vial retaining hole 15 of the first turntable 14. On the other hand, when the swivel actuator 28 swivels clockwise from the vial chucking position, the assay vial 21 is supplied to the vial retaining hole 22 of the second turntable 20. The chucking finger 29 is designed so as to travel to positions above particular parts of the peripheral portions of the first and second turntables 14 and 20. That is, the chucking finger 29 is capable of traveling vertically as well as horizontally in an R-θ direction within a horizontal plane including the aforesaid positions like a polar coordinates robot.

Figure 6:
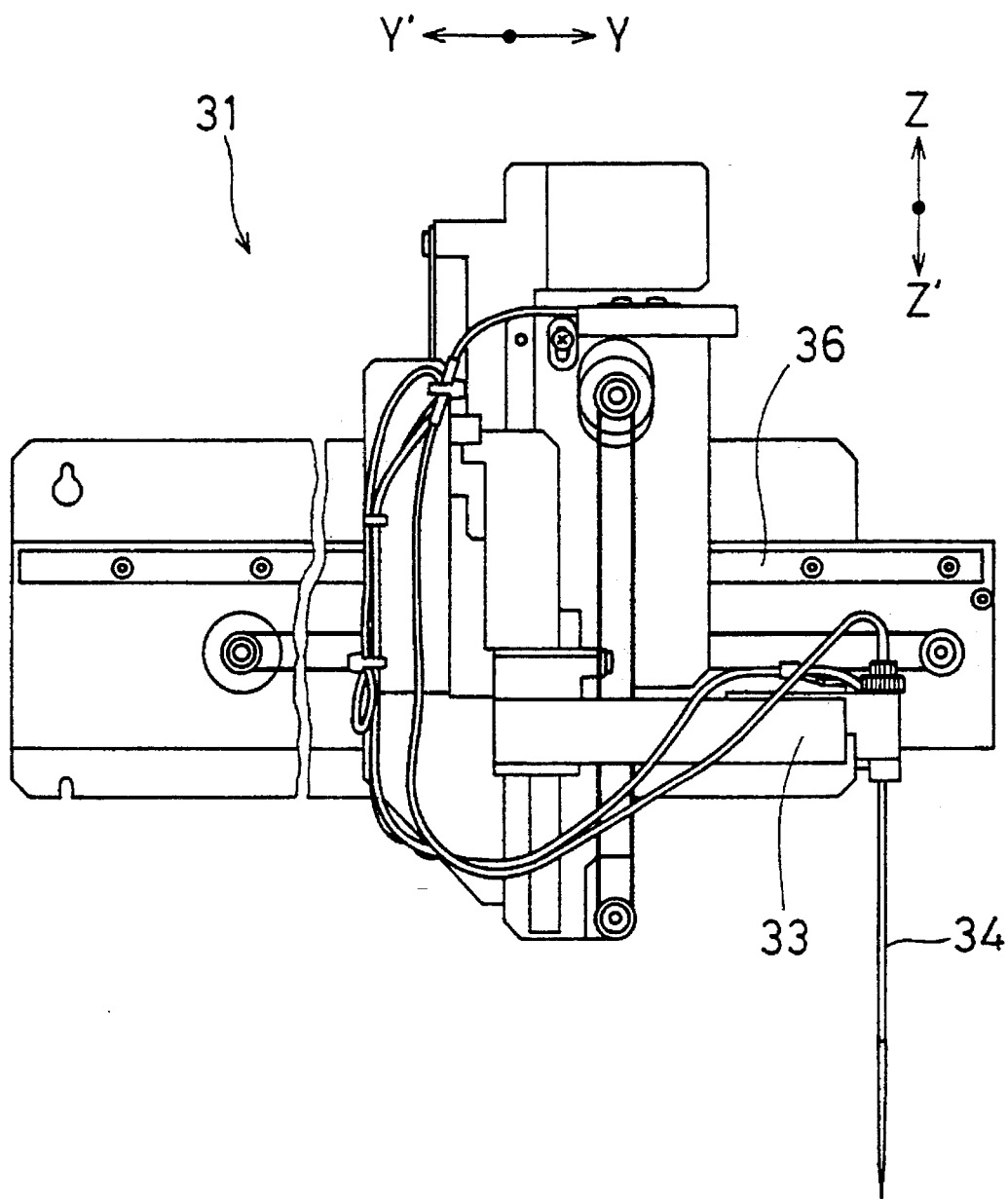
FIG. 6 is a side view illustrating second dispensing means.

On the left side of the vial distributing/supplying device 30 in FIG. 1 is disposed second dispensing device 31 for aspirating part of a specimen in a stock vial 8 and dispensing the specimen to an assay vial 21. As shown in FIG. 6, the second dispensing device 31 has an arm 33 movable in a vertical direction Z–Z', and a sampling probe 34 attached at a free end of the arm 33. The sampling probe 34 is connected to a constant-volume liquid transportation device 35 via a tube.

The second dispensing device 31 is guided by guide rails 36 to travel in a direction Y–Y', so that the sampling probe 34 reciprocates between a vial retaining hole 15 in a predetermined position of the first turntable 14 and a via retaining hole 22 in a predetermined position of the second turntable 20.

A container of a diluent (not shogun) is provided between the first turntable 14 and the second turntable 20. On the way to travel between the vial retaining holes 15 and 22, the sampling probe 34 aspirates the diluent, so that a mixture of the specimen and the diluent is supplied in an assay vial 21.

Figure 7:
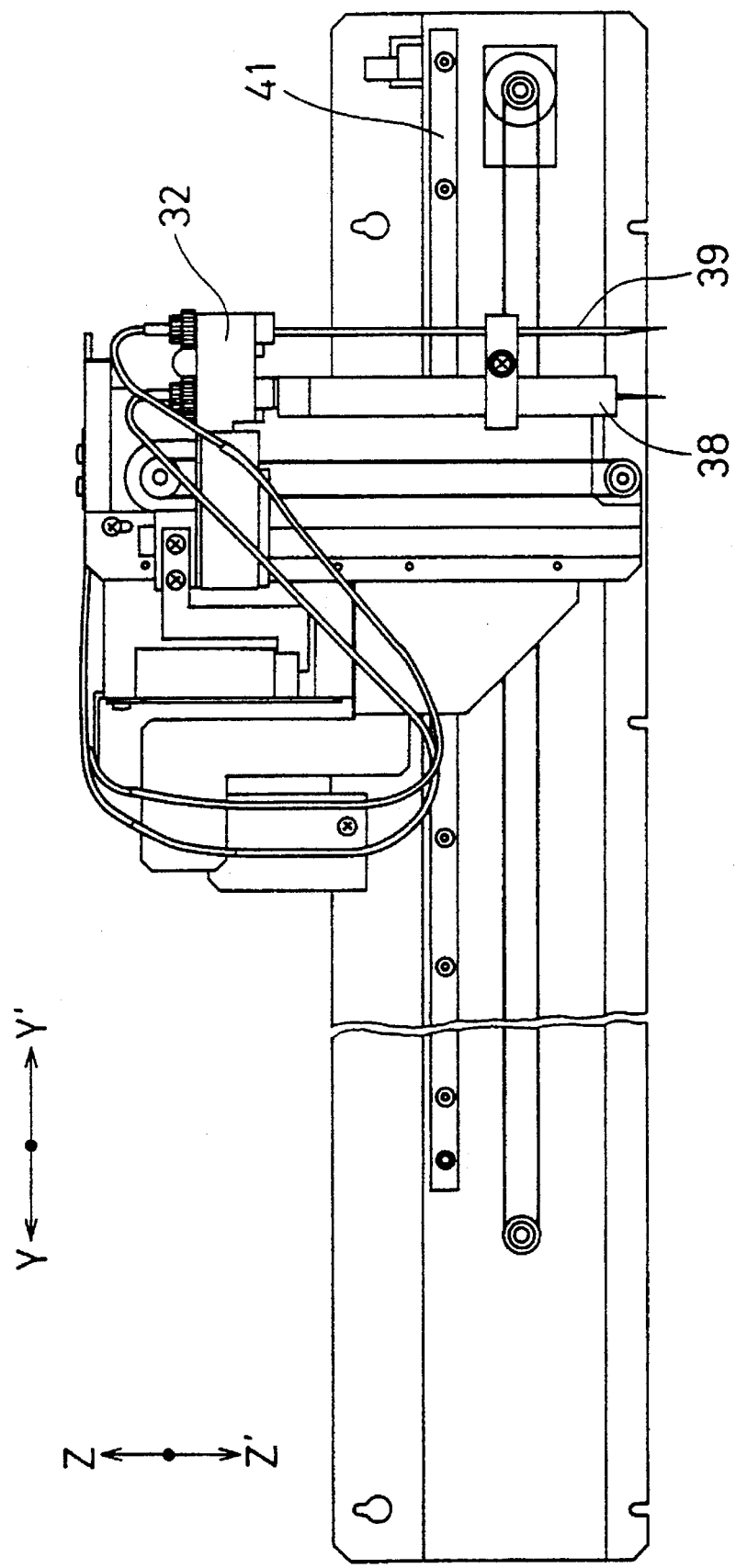
FIG. 7 is a side view illustrating reagent dispensing means.

On the right side of the vial distributing/supplying device 30 in FIG. 1 is provided reagent dispensing device 37 for aspirating predetermined amounts of reagents in the reagent containers 16 and 17 and dispensing the reagents into the assay vial 21. As shown in FIG. 7, the reagent dispensing means 37 has an arm 32 movable in a vertical direction Z–Z', and two sampling probes 38 and 39 attached at a free end of the arm 32. The sampling probes 38 and 39 are connected to a constant-volume liquid transportation device 40 via tubes.

The reagent dispensing device 37 is guided by guide rails 41 to travel in a direction Y–Y', so that the sampling probes 38 and 39 reciprocate between a reagent mixing position (below the sampling probe 38) of the chucking finger 29 (FIG. 5) and the reagent container retaining holes 18 and 19 in predetermined positions of the first turntable 14.

Adjacent to the second turntable 20 are disposed four assay stages 42 for assaying specimens in assay vials 21, as shown in FIG. 1. The assay stages 42 are each formed with four assay holes 43 for accommodating the assay vials 21, and an analysis device 52 for optically analyzing a specimen is provided near the bottom of each of the assay holes 43. More specifically, the characteristics of the specimen are determined by the measurement of scattered light intensity or transmittance, in which light is emitted to the specimen from the lateral side thereof.

Above the assay stage 42 are provided two movable guide rails 44 and 45 horizontally extending in a direction X–X'. The movable guide rails 44 and 45 are movably attached on stationary guide rails 46 and 47 extending perpendicular to the movable guide rails 44 and 45 (in a direction Y–Y'). On the movable guide rails 44 and 45 is mounted a vial transporting device 51 for vibrating the assay vial 21 at the reagent mixing position to mix the reagents with the specimen and transporting the assay vial 21 to a predetermined assay hole 43 of the assay stage 42. The vial transporting device 51 has a vertically movable chucking finger 48 which is the same type as the chucking finger 29 in the vial distributing/supplying device 30.

More specifically, the chucking finger 48 is capable of traveling vertically in a direction Z–Z' as well as horizontally within a horizontal plane in directions X–x' and Y–Y'like an orthogonal coordinates robot, and stops at locations above a particular part of the peripheral portion of the second turntable 20, the reagent mixing position and the assay stage 42.

In the proximal portion of the chucking finger 48 is provided a vibration motor (not shown) for vibrating the assay vial 21 to fully mix the reagents with the specimen in the assay vial 21.

Figure 8:
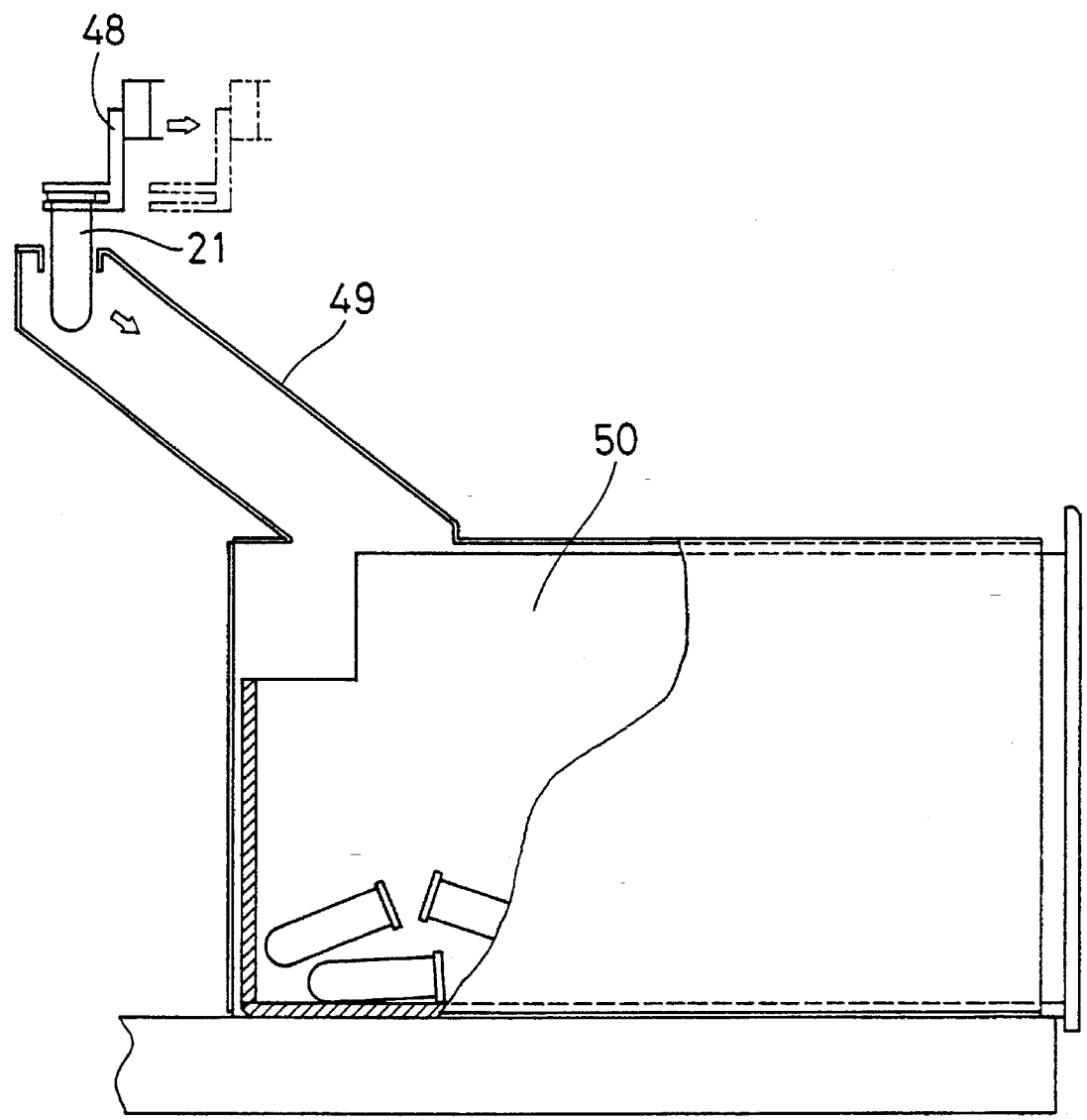
FIG. 8 is a side view illustrating a used vial collecting box.

A vial discharging chute 49 for discharging assay vials 21 after the assay is provided on a lower left side of the assay stages 42 as shown in FIG. 1. A used vial collecting box 50 for collecting used assay vials 21 after the assay is detachably attached to a lower end of the vial discharging chute 49 as shown in FIG. 8.

Figure 9:
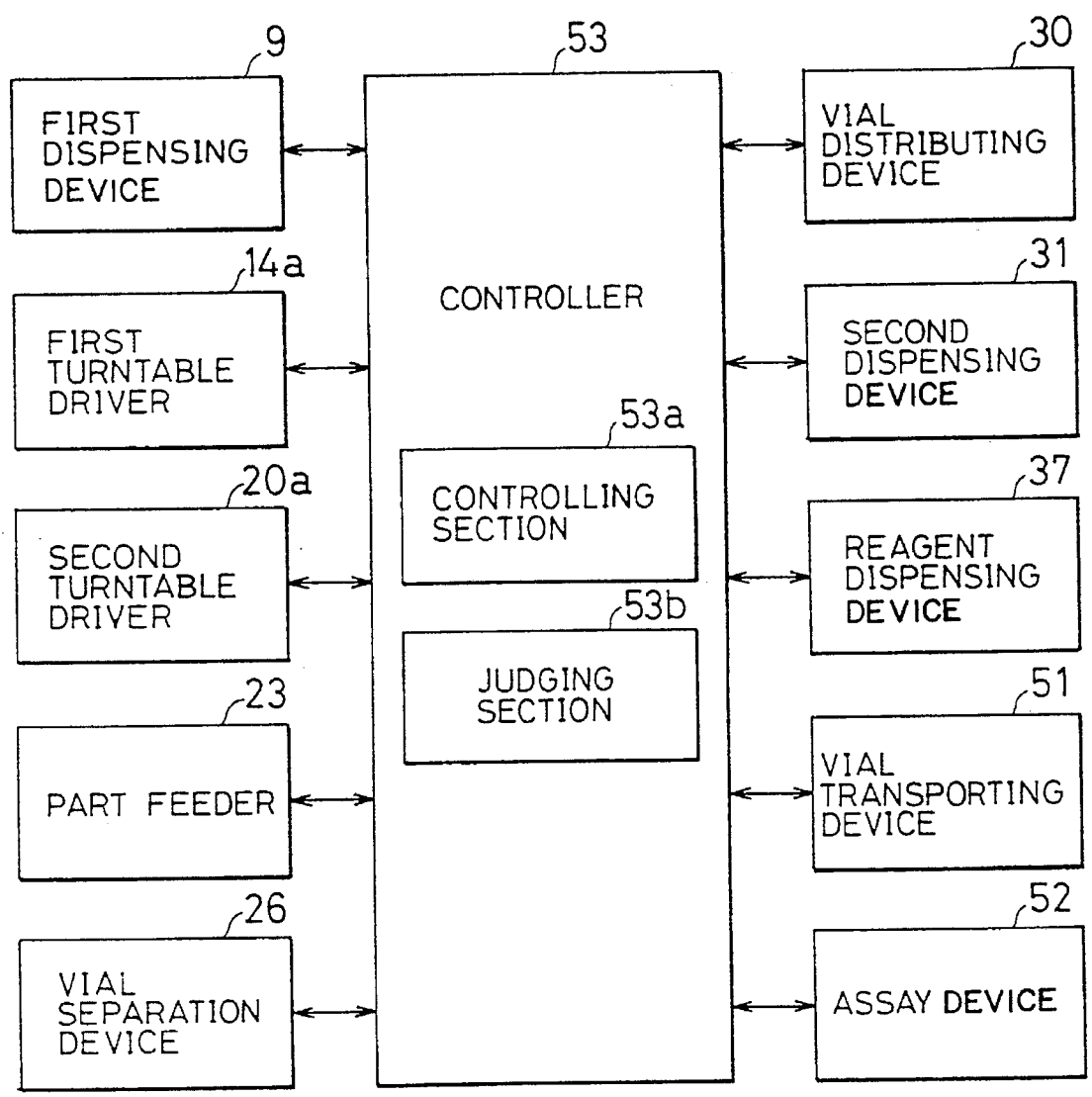
FIG. 9 is a block diagram illustrating a control circuit according to the embodiment of the present invention.

FIG. 9 is a block diagram illustrating a control circuit in accordance with this embodiment. As shown, a controller 53 including a CPU, a ROM and a RAM includes a controlling section 53a for controlling the first dispensing device 9, a driver 14a for the first turntable 14, a driver 20a for the second turntable 20, the part feeder 23, the vial separation device 26, the vial distributing device 30, the second dispensing device 31, the reagent dispensing device 37, the vial transporting device 51 and the assay device 52, and a judging section 53b for judging whether the assay is to be performed again on the same specimen based on an assay result and predetermined assay conditions.

Figure 10:
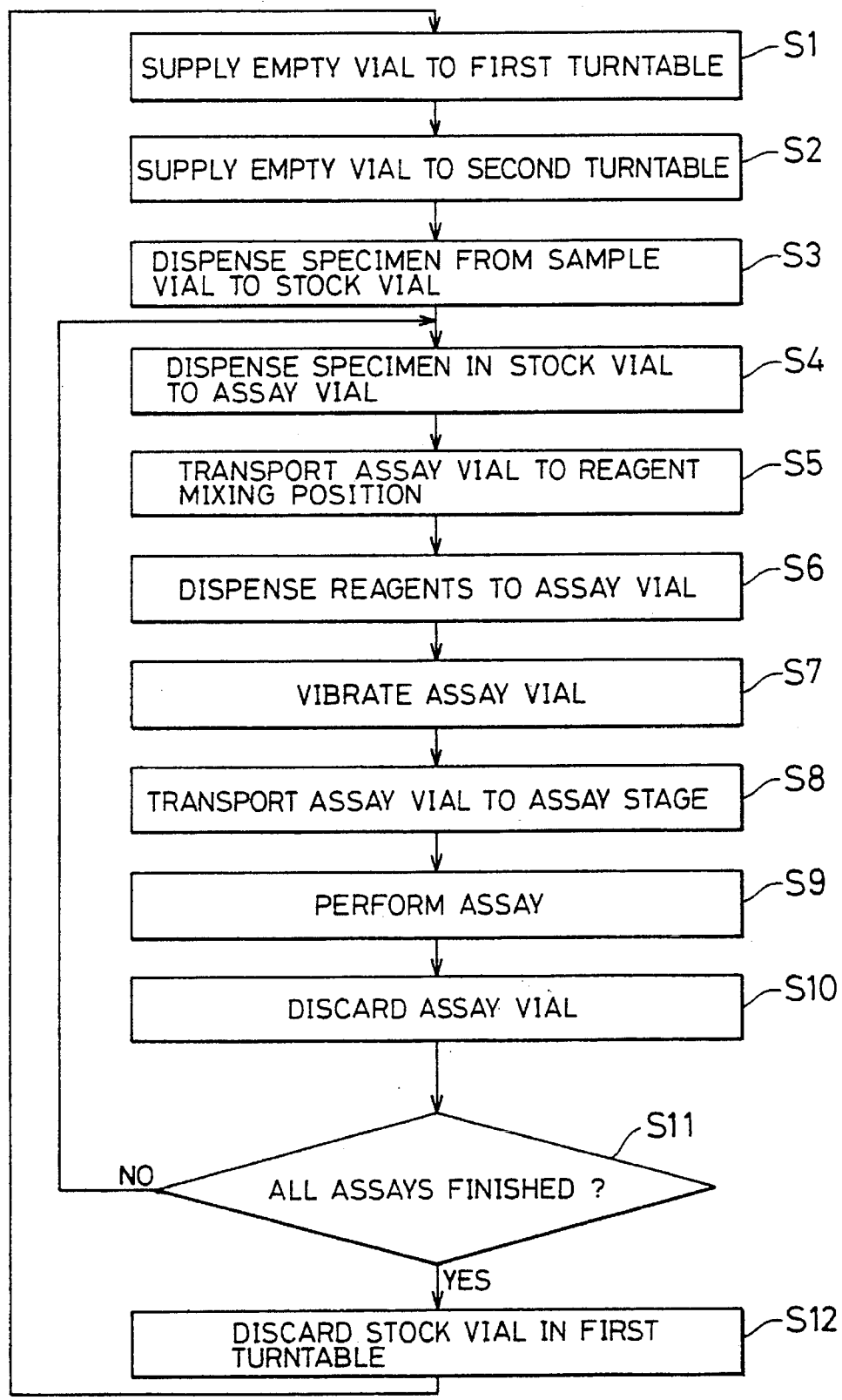
FIG. 10 is a flow chart illustrating a process sequence according to the embodiment of the present invention.

An explanation will be given to a process sequence according to this embodiment with reference to a flow chart shown in FIG. 10.

The vial distributing/supplying device 30 successively supplies stock vials 8 into the vial retaining holes 15 of the first turntable 14 (Step S1). The vial distributing/supplying device 30 successively supplies assay vials 21 into the vial retaining holes 22 of the second turntable 20 after supplying the stock vials 8 (Step S2). Otherwise, the stock vials 8 and assay vials 21 may be alternately supplied. The first dispensing means 9 aspirates, for example, 100 μl to 500 μl of a specimen in each sample vial 4 and dispenses the specimen into a stock vial 8 in a vial retaining hole 15 (Step S3). The amount T of the specimen to be dispensed is determined on the basis of a volume necessary for one measurement (S1+S2+. . . +Sn), the number (k) of measurements, and a spare volume (U) as previously stated. The dispensing of the specimens is controlled so that the sample vials 4 and the stock vials 8 have an exact one-to-one correspondence with each other.

The second dispensing means 31 aspirates, for example, 5 μl to 100 μl of the specimen in the stock vial 8, then aspirates a predetermined amount of a diluent for dilution of the specimen if necessary, and dispenses the diluted specimen into the assay vial 21 (Step S4). Accordingly, a certain amount of the specimen remains in the stock vial 8.

The chucking finger 48 holds the assay vial 21 containing the diluted specimen and transports the assay vial 21 from the vial retaining hole 22 of the second turntable 20 to the reagent mixing position (Step S5). At this time, the reagent dispensing means 37 aspirates a predetermined reagent, then travels to the reagent mixing position, and dispenses the reagent into the assay vial 21 (Step S6). During and after the dispensing of the reagent, the vibration motor vibrates the chucking finger 48 holding the assay vial 21 to fully mix the reagent with the specimen in the assay vial 21 (Step S7). Thereafter, the assay vial 21 is inserted into a predetermined assay hole 43 and the specimen is subjected to an assay (Steps S8 and S9). The time required for an assay varies depending on the assay category and, typically, is three minutes to ten minutes. It should be noted that the reagent dispensing means 37 has two sampling probes 38 and 39, which are selectively used depending on the kind of reagent to be used and the assay category.

The used assay vial 21 is transported to the vial discharging chute 49 by the chucking finger 48 and collected into the used vial collecting box 50 (Step S10). If a plurality of assays such as for PT and APTT are to be performed or a reflex test is to be performed (step S11), the judging section 53b causes the process sequence after the dispensing of the specimen by the second dispensing means 31 (Steps S4 to S10) to be repeated a predetermined number of times. In such a case, different kinds of reagents may be used in different amounts, depending on the assay to be performed.

Further, if the judging section 53b judges in Step S11 that the assay result on the specimen is within a predetermined abnormal value range or out of a predetermined normal value range (or the specimen has to be re-assayed), the first turntable 14 is rotated and the stock vial 8 containing the specimen is automatically selected. Then, the specimen is assayed again by following the aforesaid process sequence. That is, the specimen is dispensed into an assay vial 21, then the reagent is added thereto, and the assay is performed again on the specimen.

After all the specimens on the first turntable 14 are correctly assayed and the assay process is completed, the vial distributing/supplying device 30 temporality transfers the stock vials 8 on the first turntable 14 into the vial retaining holes 22 of the second turntable 20. Then, the chucking finger 48 transfers the stock vials 8 from the second turntable 20 to the used vial collecting box 50 (Step S12).

When the assay is performed again, the mount of the diluent to be dispensed can be properly adjusted. More specifically, when the assay result is out of an effective accuracy range due to a high or low concentration of the specimen, the dilution may be increased or decreased so as to adjust the concentration of the specimen for the re-assay.

In this embodiment, the stock vials 8 are cooled to a temperature of 15° C. as described above. Therefore, the specimens will not evaporate even if the specimen is left in the vial 8 for a long time before the assay.

Since the specimen is not directly dispensed from the sample vial 4 to the assay vial 21, such problems as wear of the sample probe, contamination by a rubber scum and inaccurate dispense volume can be eliminated which may otherwise be caused by the rubber stopper fixed to the sample vial 4. Sample vials capped with no rubber stopper can, of course, be employed in the present invention.

In accordance with the present invention, a specimen in a stock vial can be used for plural measurements or plural assays by dispensing the specimen from the stock vial into an assay vial plural times. Even if a sample vial containing the specimen is transported to the next process, the re-assay of the specimen can be easily performed. This realizes a more effective re-assay.

Further, the apparatus of the present invention has a simpler and smaller-scale construction, and thereby less costly, in comparison with an analyzer adapted to return a rack accommodating a necessary sample vial thereto every time a re-assay is to be performed.

In addition, since the stock vial is cooled, the specimen contained therein will not evaporate nor deteriorate.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for automatically analyzing a specimen, comprising:

sample vial retaining means for retaining a sample vial containing a specimen;

a stock vial into which part of the specimen in the sample vial is to be dispensed;

stock vial retaining means for retaining a stock vial;

first dispensing means for dispensing the specimen in the sample vial into the stock vial;

an assay vial into which part of the specimen in the stock vial is to be dispensed;

assay vial retaining means for retaining a plurality of assay vials;

second dispensing means for dispensing the specimen in the stock vial into the assay vial;

a reagent container for containing a reagent;

third dispensing means for dispensing the reagent into the assay vial;

assay means for assaying the specimen in the assay vial;

assay vial transporting means for transporting the assay vial from the assay vial retaining means to the assay means;

vial discharging means for discharging the assay vial after the assay; and a controller for controlling the sample vial retaining means, the stock vial retaining means, the first dispensing means, the assay vial retaining means, the second dispensing means, the third dispensing means, the assay means, the assay vial transporting means, and the vial discharging means, whereby the specimen, once dispensed from the sample vial into the stock vial, is dispensed from the stock vial into the assay vial for the assay throughout the automatic analysis.

2. An apparatus as set forth in claim 1, wherein the controller comprises a judging section for making a judgement on a result of the assay, and controls the respective means so as to dispense the specimen from the stock vial containing the specimen into another assay vial to re-assay the specimen, based on the judgement made by the judging section.

3. An apparatus as set forth in claim 2, wherein if the judging section judges that the result of the assay is out of a predetermined range, the controller controls the respective means so as to dispense the specimen from the stock vial containing the specimen into another assay vial to re-assay the specimen.

4. An apparatus as set forth in claim 2, wherein if the judging section judges that a number of measurements for the assay does not reach a predetermined number, the controller controls the respective means so as to dispense the specimen from the stock vial containing the specimen into another assay vial to re-assay the specimen.

5. An apparatus as set forth in claim 1, wherein the stock vial and the assay vial have the same configuration.

6. An apparatus as set forth in claim 1 further comprising vial supplying means for supplying the stock vial and the assay vial to the stock vial retaining means and assay vial retaining means, respectively.

7. An apparatus as set forth in claim 1, wherein the stock vial retaining means retains the reagent containers.

8. An apparatus as set forth in claim 1, wherein the stock vial retaining means and the assay vial retaining means are provided with cooling means and incubating means, respectively.

9. An apparatus as set forth in claim 1, wherein the stock vial retaining means is a disk-shaped turntable formed with vial retaining holes annularly aligned thereon.

10. An apparatus as set forth in claim 1, wherein the sample vial is closed with a soft stopper, and the first dispensing means is provided with means for sticking the stopper to aspirate the specimen contained in the sample vial.

11. An apparatus as set forth in claim 1, wherein the specimen includes blood plasma.

12. An apparatus as set forth in claim 1, wherein the specimen includes urine.

13. An apparatus as set forth in claim 1, further comprising means for adjusting a concentration of a specimen to be re-assayed in an assay vial in accordance with a result of a previous assay of said specimen.

* * * * *